(12) United States Patent
Penner et al.

(10) Patent No.: US 7,621,905 B2
(45) Date of Patent: Nov. 24, 2009

(54) DEVICES FOR INTRABODY DELIVERY OF MOLECULES AND SYSTEMS AND METHODS UTILIZING SAME

(75) Inventors: Avi Penner, Tel Aviv (IL); Eyal Doron, Kiryat Yam (IL)

(73) Assignee: Remon Medical Technologies Ltd., Caesarea (IL)

( * ) Notice: Subject to any disclaimer, the term of this patent is extended or adjusted under 35 U.S.C. 154(b) by 1587 days.

(21) Appl. No.: 10/638,405

(22) Filed: Aug. 12, 2003

(65) Prior Publication Data

US 2004/0032187 A1 Feb. 19, 2004
US 2008/0191581 A9 Aug. 14, 2008

Related U.S. Application Data

(63) Continuation of application No. 09/930,455, filed on Aug. 16, 2001, now abandoned, and a continuation-in-part of application No. 10/235,968, filed on Sep. 6, 2002, now Pat. No. 6,720,709, which is a continuation of application No. 09/691,887, filed on Oct. 20, 2000, now Pat. No. 6,504,286, which is a continuation of application No. 09/000,553, filed on Dec. 30, 1997, now Pat. No. 6,140,740.

(51) Int. Cl.
*A61K 9/22* (2006.01)
(52) U.S. Cl. .................................... 604/891.1
(58) Field of Classification Search .............. 604/891.1; 310/311
See application file for complete search history.

(56) References Cited

U.S. PATENT DOCUMENTS

| | | | |
|---|---|---|---|
| 3,310,885 A | 3/1967 | Alderson | |
| 3,320,946 A | 5/1967 | Dethloff et al. | |
| 3,536,836 A | * 10/1970 | Pfeiffer | ............... 200/61.01 |
| 3,568,661 A | 3/1971 | Franklin | |
| 3,672,352 A | 6/1972 | Summers | |
| 3,692,027 A | 9/1972 | Ellinwood | |
| 3,757,770 A | 9/1973 | Brayshaw et al. | |
| 3,794,840 A | 2/1974 | Scott | |
| 3,868,578 A | 2/1975 | Oldham | |
| 3,943,915 A | 3/1976 | Severson | |
| 4,003,379 A | 1/1977 | Ellinwood | |
| 4,041,954 A | 8/1977 | Ohara | |
| 4,127,110 A | 11/1978 | Bullara | |
| 4,146,029 A | 3/1979 | Ellinwood | |
| 4,223,801 A | 9/1980 | Carlson | |

(Continued)

FOREIGN PATENT DOCUMENTS

EP 0897690 2/1999

(Continued)

*Primary Examiner*—Nicholas D Lucchesi
*Assistant Examiner*—Victoria P Campbell
(74) *Attorney, Agent, or Firm*—Faegre & Benson LLP

(57) ABSTRACT

A device for controlled release of molecules is provided. The device including: (a) a device body having at least one reservoir therein for containing the molecules, the at least one reservoir being formed with a barrier impermeable to the molecules thereby preventing release thereof from the at least one reservoir; and (b) at least one acoustic transducer being attached to, or forming a part of, the device body, the at least one acoustic transducer being for converting an acoustic signal received thereby into an electrical signal, the electrical signal leading to barrier permeabilization and therefore release of the molecules from the at least one reservoir.

16 Claims, 4 Drawing Sheets

U.S. PATENT DOCUMENTS

| | | |
|---|---|---|
| 4,227,407 A | 10/1980 | Drost |
| 4,237,900 A | 12/1980 | Schulman et al. |
| 4,281,664 A | 8/1981 | Duggen |
| 4,360,019 A | 11/1982 | Portner et al. |
| 4,407,296 A | 10/1983 | Anderson |
| 4,450,527 A | 5/1984 | Sramek |
| 4,480,483 A | 11/1984 | McShane |
| 4,519,401 A | 5/1985 | Ko et al. |
| 4,541,431 A | 9/1985 | Ibrahim et al. |
| 4,543,955 A | 10/1985 | Schroeppel |
| 4,550,370 A | 10/1985 | Baker |
| 4,583,553 A | 4/1986 | Shah et al. |
| 4,585,004 A | 4/1986 | Brownlee |
| 4,593,703 A | 6/1986 | Cosman |
| 4,600,855 A | 7/1986 | Strachan |
| 4,616,640 A | 10/1986 | Kaali et al. |
| 4,651,740 A | 3/1987 | Schroeppel |
| 4,653,508 A | 3/1987 | Cosman |
| 4,660,568 A | 4/1987 | Cosman |
| 4,676,255 A | 6/1987 | Cosman |
| 4,677,985 A | 7/1987 | Bro et al. |
| 4,680,957 A | 7/1987 | Dodd |
| 4,686,987 A | 8/1987 | Salo et al. |
| 4,697,595 A | 10/1987 | Breyer et al. |
| 4,716,903 A | 1/1988 | Hansen et al. |
| 4,726,380 A | 2/1988 | Vollmann et al. |
| 4,768,176 A | 8/1988 | Kehr et al. |
| 4,768,177 A | 8/1988 | Kehr et al. |
| 4,781,715 A | 11/1988 | Wurzel |
| 4,791,936 A | 12/1988 | Snell et al. |
| 4,793,827 A | 12/1988 | Kovacs et al. |
| 4,809,697 A | 3/1989 | Causey, III et al. |
| 4,814,974 A | 3/1989 | Narayanan et al. |
| 4,845,503 A | 7/1989 | Adam et al. |
| 4,846,191 A | 7/1989 | Brockway et al. |
| 4,854,327 A | 8/1989 | Kunig |
| 4,899,752 A | 2/1990 | Cohen |
| 4,909,259 A | 3/1990 | Tehrani |
| 4,920,489 A | 4/1990 | Hubelbank et al. |
| 4,945,477 A | 7/1990 | Edwards |
| 4,945,914 A | 8/1990 | Allen |
| 4,967,749 A | 11/1990 | Cohen |
| 4,986,270 A | 1/1991 | Cohen |
| 4,991,579 A | 2/1991 | Allen |
| 4,995,068 A | 2/1991 | Chou et al. |
| 4,995,398 A | 2/1991 | Turnidge |
| 5,002,062 A | 3/1991 | Suzuki |
| 5,003,976 A | 4/1991 | Alt |
| 5,007,431 A | 4/1991 | Donehoo, III |
| 5,024,224 A | 6/1991 | Engebretson |
| 5,025,795 A | 6/1991 | Kunig |
| 5,029,582 A | 7/1991 | Lekholm |
| 5,040,536 A | 8/1991 | Riff |
| 5,040,538 A | 8/1991 | Mortazavi |
| 5,052,399 A | 10/1991 | Olive et al. |
| 5,113,859 A | 5/1992 | Funke |
| 5,154,171 A | 10/1992 | Chirife |
| 5,161,536 A | 11/1992 | Vilkomerson et al. |
| 5,163,429 A | 11/1992 | Cohen |
| 5,178,151 A | 1/1993 | Sackner |
| 5,178,153 A | 1/1993 | Einzig |
| 5,190,035 A | 3/1993 | Salo et al. |
| 5,199,428 A | 4/1993 | Obel et al. |
| 5,200,891 A | 4/1993 | Kehr et al. |
| 5,213,098 A | 5/1993 | Bennett et al. |
| 5,215,098 A | 6/1993 | Steinhaus et al. |
| 5,217,021 A | 6/1993 | Steinhaus et al. |
| 5,246,008 A | 9/1993 | Mueller |
| 5,263,486 A | 11/1993 | Jeffreys |
| 5,267,174 A | 11/1993 | Kaufman et al. |
| 5,277,191 A | 1/1994 | Hughes |
| 5,279,309 A | 1/1994 | Taylor et al. |
| 5,279,607 A | 1/1994 | Schentag et al. |
| 5,289,821 A | 3/1994 | Swartz |
| 5,300,092 A | 4/1994 | Schaldach |
| 5,309,919 A | 5/1994 | Snell et al. |
| 5,312,446 A | 5/1994 | Holschbach et al. |
| 5,313,953 A | 5/1994 | Yomtov et al. |
| 5,314,457 A | 5/1994 | Jeutter et al. |
| 5,329,459 A | 7/1994 | Kaufman et al. |
| 5,330,505 A | 7/1994 | Cohen |
| 5,331,966 A | 7/1994 | Bennett et al. |
| 5,339,051 A | 8/1994 | Koehler et al. |
| 5,354,316 A | 10/1994 | Keimel |
| 5,360,440 A | 11/1994 | Andersen |
| 5,368,040 A | 11/1994 | Carney |
| 5,375,603 A | 12/1994 | Feiler |
| 5,394,457 A | 2/1995 | Leibinger et al. |
| 5,397,329 A | 3/1995 | Allen |
| 5,411,535 A | 5/1995 | Fujii et al. |
| 5,411,551 A | 5/1995 | Winston et al. |
| 5,417,717 A | 5/1995 | Salo et al. |
| 5,423,334 A | 6/1995 | Jordan |
| 5,438,990 A | 8/1995 | Wahlstrand et al. |
| 5,442,351 A | 8/1995 | Horspool et al. |
| 5,445,608 A | 8/1995 | Chen et al. |
| 5,454,838 A | 10/1995 | Vallana et al. |
| 5,458,627 A | 10/1995 | Baranowski, Jr. et al. |
| 5,469,859 A | 11/1995 | Tsoglin et al. |
| 5,476,488 A | 12/1995 | Morgan et al. |
| 5,488,954 A * | 2/1996 | Sleva et al. .................. 600/459 |
| 5,490,962 A | 2/1996 | Cima et al. |
| 5,507,780 A | 4/1996 | Finch |
| 5,509,424 A | 4/1996 | Al-Ali |
| 5,518,001 A | 5/1996 | Snell |
| 5,528,067 A | 6/1996 | Farb |
| 5,535,752 A | 7/1996 | Halperin et al. |
| 5,545,186 A | 8/1996 | Olson et al. |
| 5,558,091 A | 9/1996 | Acker et al. |
| 5,562,714 A | 10/1996 | Grevious |
| 5,564,434 A | 10/1996 | Halperin et al. |
| 5,571,152 A | 11/1996 | Chen et al. |
| 5,603,331 A | 2/1997 | Heemels et al. |
| 5,604,531 A | 2/1997 | Iddan et al. |
| 5,619,997 A | 4/1997 | Kaplan |
| 5,623,935 A | 4/1997 | Faisandier |
| 5,626,630 A | 5/1997 | Markowitz et al. |
| 5,628,782 A | 5/1997 | Myers |
| 5,642,731 A | 7/1997 | Kehr |
| 5,643,327 A | 7/1997 | Dawson et al. |
| 5,656,428 A | 8/1997 | McAllister et al. |
| 5,704,352 A | 1/1998 | Tremblay et al. |
| 5,705,753 A | 1/1998 | Hastings et al. |
| 5,709,216 A | 1/1998 | Woodson, III |
| 5,728,281 A | 3/1998 | Holstrom et al. |
| 5,729,129 A | 3/1998 | Acker |
| 5,732,708 A | 3/1998 | Nau et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,749,909 A | 5/1998 | Schroeppel et al. |
| 5,752,235 A | 5/1998 | Kehr et al. |
| 5,752,976 A | 5/1998 | Duffin et al. |
| 5,755,766 A | 5/1998 | Chastain et al. |
| 5,769,877 A | 6/1998 | Barreras, Sr. |
| 5,772,999 A | 6/1998 | Greenblatt et al. |
| 5,776,168 A | 7/1998 | Gunderson |
| 5,776,324 A | 7/1998 | Usala |
| 5,779,634 A | 7/1998 | Ema et al. |
| 5,785,660 A | 7/1998 | van Lake et al. |
| 5,792,195 A | 8/1998 | Carlson et al. |
| 5,796,827 A | 8/1998 | Coppersmith et al. |
| 5,797,898 A * | 8/1998 | Santini et al. ............. 604/890.1 |
| 5,800,478 A | 9/1998 | Chen et al. |

| | | | | | | |
|---|---|---|---|---|---|---|
| 5,804,258 | A | 9/1998 | Lohwasser et al. | 6,277,078 B1 | 8/2001 | Porat et al. |
| 5,807,258 | A | 9/1998 | Cimochowski et al. | 6,278,894 B1 | 8/2001 | Salo et al. |
| 5,807,395 | A | 9/1998 | Mulier et al. | 6,287,332 B1 | 9/2001 | Bolz et al. |
| 5,807,397 | A | 9/1998 | Barreras | 6,305,381 B1 | 10/2001 | Weijand et al. |
| 5,810,009 | A | 9/1998 | Mine et al. | 6,308,099 B1 | 10/2001 | Fox et al. |
| 5,810,735 | A | 9/1998 | Halperin et al. | 6,330,957 B1 | 12/2001 | Bell-Greenstreet |
| 5,819,740 | A | 10/1998 | Muhlenberg et al. | 6,331,163 B1 | 12/2001 | Kaplan |
| 5,832,924 | A | 11/1998 | Archibald et al. | 6,347,245 B1 | 2/2002 | Lee et al. |
| 5,833,603 | A | 11/1998 | Kovacs et al. | 6,366,808 B1 | 4/2002 | Schroeppel et al. |
| 5,833,715 | A | 11/1998 | Vachon et al. | 6,368,275 B1 | 4/2002 | Sliwa et al. |
| 5,835,455 | A | 11/1998 | Hanson et al. | 6,397,661 B1 | 6/2002 | Grimes et al. |
| 5,836,300 | A | 11/1998 | Mault | 6,409,674 B1 | 6/2002 | Brockway et al. |
| 5,836,889 | A | 11/1998 | Wyborny et al. | 6,409,675 B1 | 6/2002 | Turcott |
| 5,836,982 | A | 11/1998 | Muhlenberg et al. | 6,411,850 B1 | 6/2002 | Kay et al. |
| 5,843,089 | A | 12/1998 | Sahatijan et al. | 6,416,474 B1 | 7/2002 | Penner et al. |
| 5,843,135 | A | 12/1998 | Weijand et al. | 6,431,175 B1 | 8/2002 | Penner et al. |
| 5,855,609 | A | 1/1999 | Knapp | 6,432,050 B1 | 8/2002 | Porat et al. |
| 5,856,722 | A | 1/1999 | Haronian et al. | 6,438,408 B1 | 8/2002 | Mulligan et al. |
| 5,868,673 | A | 2/1999 | Vesely | 6,441,747 B1 | 8/2002 | Khair et al. |
| 5,873,835 | A | 2/1999 | Hastings et al. | 6,442,413 B1 | 8/2002 | Silver |
| 5,873,904 | A | 2/1999 | Ragheb et al. | 6,445,953 B1 | 9/2002 | Bulkes et al. |
| 5,880,661 | A | 3/1999 | Davidson et al. | 6,456,883 B1 | 9/2002 | Torgerson et al. |
| 5,886,267 | A | 3/1999 | Ortiz | 6,471,645 B1 | 10/2002 | Warkentin et al. |
| 5,891,180 | A | 4/1999 | Greeninger et al. | 6,472,991 B1 | 10/2002 | Schulman et al. |
| 5,904,708 | A | 5/1999 | Goedeke | 6,475,170 B1 | 11/2002 | Doron et al. |
| 5,908,392 | A | 6/1999 | Wilson et al. | 6,486,588 B2 | 11/2002 | Doron et al. |
| 5,911,685 | A | 6/1999 | Siess et al. | 6,504,286 B1 | 1/2003 | Porat et al. |
| 5,919,221 | A | 7/1999 | Miesel | 6,522,914 B1 | 2/2003 | Huvelle et al. |
| 5,935,081 | A | 8/1999 | Kadhiresan | 6,526,314 B1 | 2/2003 | Eberle et al. |
| 5,938,903 | A | 8/1999 | Broderick | 6,567,700 B1 | 5/2003 | Turcott et al. |
| 5,941,249 | A | 8/1999 | Maynard | 6,574,510 B2 | 6/2003 | Von Arx et al. |
| 5,951,458 | A | 9/1999 | Hastings et al. | 6,580,946 B2 | 6/2003 | Struble |
| 5,954,641 | A | 9/1999 | Kehr et al. | 6,584,349 B1 | 6/2003 | Sage et al. |
| 5,957,950 | A | 9/1999 | Mockros et al. | 6,584,354 B1 | 6/2003 | Mann et al. |
| 5,967,986 | A | 10/1999 | Cimochowski et al. | 6,585,764 B2 | 7/2003 | Wright et al. |
| 5,976,169 | A | 11/1999 | Imran | 6,589,187 B1 | 7/2003 | Dirnberger et al. |
| 5,980,554 | A | 11/1999 | Lenker et al. | 6,599,242 B1 | 7/2003 | Splett et al. |
| 6,002,963 | A | 12/1999 | Mouchawar et al. | 6,604,000 B2 | 8/2003 | Lu |
| 6,009,472 | A | 12/1999 | Boudou et al. | 6,607,485 B2 | 8/2003 | Bardy |
| 6,021,347 | A | 2/2000 | Herbst et al. | 6,609,023 B1 | 8/2003 | Fischell et al. |
| 6,023,641 | A | 2/2000 | Thompson | 6,615,083 B2 | 9/2003 | Kupper |
| 6,024,704 | A | 2/2000 | Meador et al. | 6,622,049 B2 | 9/2003 | Penner et al. |
| 6,053,873 | A | 4/2000 | Govari et al. | 6,622,050 B2 | 9/2003 | Thompson |
| 6,080,190 | A | 6/2000 | Schwartz | 6,628,985 B2 | 9/2003 | Sweeney et al. |
| 6,083,248 | A | 7/2000 | Thompson | 6,628,989 B1 | 9/2003 | Penner et al. |
| 6,112,116 | A | 8/2000 | Fischell et al. | 6,638,231 B2 | 10/2003 | Govari et al. |
| 6,140,740 | A | 10/2000 | Porat et al. | 6,644,322 B2 | 11/2003 | Webb |
| 6,141,588 | A | 10/2000 | Cox et al. | 6,650,939 B2 | 11/2003 | Taepke, II et al. |
| 6,152,885 | A | 11/2000 | Taepke | 6,654,638 B1 | 11/2003 | Sweeney |
| 6,155,267 | A | 12/2000 | Nelson | 6,660,034 B1 | 12/2003 | Mandrusov et al. |
| 6,161,032 | A | 12/2000 | Acker | 6,675,049 B2 | 1/2004 | Thompson et al. |
| 6,162,238 | A | 12/2000 | Kaplan et al. | 6,682,985 B2 | 1/2004 | Yuzuriha et al. |
| 6,164,284 | A | 12/2000 | Schulman et al. | 6,699,186 B1 | 3/2004 | Wolinsky et al. |
| 6,170,488 | B1 | 1/2001 | Spillman, Jr. et al. | 6,702,847 B2 | 3/2004 | DiCarlo |
| 6,171,252 | B1 | 1/2001 | Roberts | 6,708,061 B2 | 3/2004 | Salo et al. |
| 6,179,767 | B1 | 1/2001 | Ziegler et al. | 6,708,065 B2 | 3/2004 | Von Arx et al. |
| 6,185,452 | B1 | 2/2001 | Schulman et al. | 6,712,772 B2 | 3/2004 | Cohen et al. |
| 6,185,455 | B1 | 2/2001 | Loeb et al. | 6,719,689 B2 | 4/2004 | Munneke et al. |
| 6,185,457 | B1 | 2/2001 | Kroll et al. | 6,720,709 B2 | 4/2004 | Porat et al. |
| 6,198,965 | B1 | 3/2001 | Penner et al. | 6,720,887 B1 | 4/2004 | Zunti |
| 6,200,265 | B1 | 3/2001 | Walsh et al. | 6,733,447 B2 | 5/2004 | Lai et al. |
| 6,201,991 | B1 | 3/2001 | Chekanov | 6,738,671 B2 | 5/2004 | Christophersom et al. |
| 6,206,914 | B1 | 3/2001 | Soykan et al. | 6,743,173 B2 | 6/2004 | Penner et al. |
| 6,227,078 | B1 | 5/2001 | Lemmo, Jr. | 6,754,795 B2 | 6/2004 | Chen et al. |
| 6,234,973 | B1 | 5/2001 | Meador et al. | 6,764,446 B2 | 7/2004 | Wolinsky et al. |
| 6,236,889 | B1 | 5/2001 | Soykan et al. | 6,778,859 B2 | 8/2004 | Gaindorge |
| 6,237,398 | B1 | 5/2001 | Porat et al. | 6,782,810 B2 | 8/2004 | Vilo |
| 6,239,724 | B1 | 5/2001 | Doron et al. | 6,783,499 B2 | 8/2004 | Schwartz |
| 6,248,080 | B1 | 6/2001 | Miesel et al. | 6,792,308 B2 | 9/2004 | Corbucci |
| 6,253,260 | B1 | 6/2001 | Beardsley et al. | 6,792,311 B2 | 9/2004 | Fox et al. |
| 6,256,538 | B1 | 7/2001 | Ekwall | 6,805,667 B2 | 10/2004 | Christopherson et al. |
| 6,266,567 | B1 | 7/2001 | Ishikawa et al. | 6,809,507 B2 | 10/2004 | Morgan et al. |
| 6,273,904 | B1 | 8/2001 | Chen et al. | 6,823,210 B2 | 11/2004 | Eberle et al. |

| | | | | | | |
|---|---|---|---|---|---|---|
| 6,824,512 B2 | 11/2004 | Warkentin et al. | | 2004/0122484 A1 | 6/2004 | Hatlestad et al. |
| 6,840,956 B1 | 1/2005 | Wolinsky et al. | | 2004/0122486 A1 | 6/2004 | Stahmann et al. |
| 6,855,115 B2 | 2/2005 | Fonseca et al. | | 2004/0152999 A1 | 8/2004 | Cohen et al. |
| 6,859,665 B2 | 2/2005 | Ding et al. | | 2004/0172081 A1 | 9/2004 | Wang |
| 6,865,419 B2 | 3/2005 | Mulligan et al. | | 2004/0230225 A1 | 11/2004 | Penner et al. |
| 6,868,346 B2 | 3/2005 | Larson et al. | | 2005/0056539 A1 | 3/2005 | Morgan et al. |
| 6,869,404 B2 | 3/2005 | Schulhauser et al. | | 2005/0060186 A1 | 3/2005 | Blowers et al. |
| 6,871,088 B2 | 3/2005 | Chinchoy | | 2005/0065815 A1 | 3/2005 | Mazar et al. |
| 6,885,889 B2 | 4/2005 | Chinchoy | | 2005/0102002 A1 | 5/2005 | Salo et al. |
| 6,889,086 B2 | 5/2005 | Mass et al. | | 2005/0137490 A1 | 6/2005 | Scheiner et al. |
| 6,895,265 B2 | 5/2005 | Silver | | 2005/0149143 A1 | 7/2005 | Libbus et al. |
| 6,907,285 B2 | 6/2005 | Denker et al. | | 2005/0154321 A1 | 7/2005 | Wolinsky et al. |
| 6,910,084 B2 | 6/2005 | Augustijn et al. | | 2005/0159789 A1 | 7/2005 | Brockway et al. |
| 6,915,162 B2 | 7/2005 | Noren et al. | | 2005/0182330 A1 | 8/2005 | Brockway et al. |
| 6,926,670 B2 | 8/2005 | Rich et al. | | 2005/0187482 A1 | 8/2005 | O'Brien et al. |
| 6,937,900 B1 | 8/2005 | Pianca et al. | | 2005/0192637 A1 | 9/2005 | Girouard et al. |
| 6,949,075 B2 | 9/2005 | Hatlestad et al. | | 2005/0192844 A1 | 9/2005 | Esler et al. |
| 6,961,448 B2 | 11/2005 | Nichols et al. | | 2005/0197585 A1 | 9/2005 | Brockway et al. |
| 6,961,617 B1 | 11/2005 | Snell | | 2005/0215887 A1 | 9/2005 | Ben-Haim et al. |
| 6,970,742 B2 | 11/2005 | Mann et al. | | 2005/0222631 A1 | 10/2005 | Dalal et al. |
| 6,978,182 B2 | 12/2005 | Mazar et al. | | 2005/0231374 A1 | 10/2005 | Diem et al. |
| 6,985,773 B2 | 1/2006 | Von Arx et al. | | 2005/0242479 A1 | 11/2005 | Petisce et al. |
| 6,993,393 B2 | 1/2006 | Von Arx et al. | | 2005/0288727 A1 | 12/2005 | Penner |
| 7,003,350 B2 | 2/2006 | Denker et al. | | 2006/0031378 A1 | 2/2006 | Vallapureddy et al. |
| 7,016,721 B2 | 3/2006 | Lee et al. | | 2006/0064133 A1 | 3/2006 | Von Arx et al. |
| 7,018,336 B2 | 3/2006 | Enegren et al. | | 2006/0064134 A1 | 3/2006 | Mazar et al. |
| 7,024,248 B2 | 4/2006 | Penner et al. | | 2006/0064142 A1 | 3/2006 | Chavan et al. |
| 7,027,872 B2 | 4/2006 | Thompson | | 2006/0064143 A1 | 3/2006 | Von Arx et al. |
| 7,033,322 B2 | 4/2006 | Silver | | 2006/0085039 A1 | 4/2006 | Hastings et al. |
| 7,035,684 B2 | 4/2006 | Lee | | 2006/0085041 A1 | 4/2006 | Hastings et al. |
| 7,047,065 B2 | 5/2006 | Kalgren et al. | | 2006/0085042 A1 | 4/2006 | Hastings et al. |
| 7,060,030 B2 | 6/2006 | Von Arx et al. | | 2006/0089694 A1 | 4/2006 | Zhang et al. |
| 7,061,381 B2 | 6/2006 | Forcier et al. | | 2006/0136004 A1 | 6/2006 | Cowan et al. |
| 7,088,254 B2 | 8/2006 | Liebenow | | 2007/0043394 A1 | 2/2007 | Zhang et al. |
| 7,127,290 B2 | 10/2006 | Girouard et al. | | 2007/0049977 A1 | 3/2007 | Von Arx et al. |
| 7,130,678 B2 | 10/2006 | Ritscher et al. | | 2007/0060959 A1 | 3/2007 | Salo et al. |
| 7,134,999 B2 | 11/2006 | Brauker et al. | | 2007/0129765 A1 | 6/2007 | Gilkerson et al. |
| 7,136,703 B1 | 11/2006 | Cappa et al. | | 2007/0142727 A1 | 6/2007 | Zhang et al. |
| 7,160,252 B2 | 1/2007 | Cho et al. | | 2008/0015421 A1 | 1/2008 | Penner |
| 7,195,594 B2 | 3/2007 | Eigler et al. | | 2008/0021333 A1 | 1/2008 | Huelskamp |
| 7,198,603 B2 | 4/2007 | Penner et al. | | 2008/0021972 A1 | 1/2008 | Huelskamp et al. |
| 7,200,439 B2 | 4/2007 | Zdeblick et al. | | 2008/0058651 A1 | 3/2008 | Shen et al. |
| 7,203,545 B2 | 4/2007 | Schmitt et al. | | 2008/0071178 A1 | 3/2008 | Greenland et al. |
| 7,204,798 B2 | 4/2007 | Zdeblick et al. | | 2008/0077440 A1 | 3/2008 | Doron |
| 7,212,861 B1 | 5/2007 | Park et al | | | | |
| 7,214,189 B2 | 5/2007 | Zdeblick | | | FOREIGN PATENT DOCUMENTS | |
| 7,225,030 B2 | 5/2007 | Kroll et al. | | | | |
| 7,236,821 B2 | 6/2007 | Cates et al. | | EP | 0928598 | 7/1999 |
| 7,248,923 B2 | 7/2007 | Maile et al. | | EP | 1266606 | 12/2002 |
| 7,273,457 B2 | 9/2007 | Penner | | EP | 1169085 | 8/2004 |
| 7,294,105 B1 | 11/2007 | Islam | | WO | WO83/03345 | 10/1983 |
| 7,335,161 B2 | 2/2008 | Von Arx et al. | | WO | WO97/01986 | 1/1997 |
| 7,392,090 B2 | 6/2008 | Sweeney et al. | | WO | WO97/32519 | 9/1997 |
| 7,399,313 B2 | 7/2008 | Brown et al. | | WO | WO97/33513 | 9/1997 |
| 7,425,200 B2 | 9/2008 | Brockway et al. | | WO | WO97/47236 | 12/1997 |
| 7,452,334 B2 | 11/2008 | Gianchandani et al. | | WO | WO98/26716 | 6/1998 |
| 7,481,771 B2 | 1/2009 | Fonseca et al. | | WO | WO98/29030 | 7/1998 |
| 2002/0023123 A1 | 2/2002 | Madison | | WO | WO99/17095 | 4/1999 |
| 2002/0042561 A1 | 4/2002 | Schulman et al. | | WO | WO99/26530 | 6/1999 |
| 2002/0045812 A1 | 4/2002 | Ben-Haim et al. | | WO | WO99/34453 | 7/1999 |
| 2002/0045836 A1 | 4/2002 | Alkawwas | | WO | WO99/47205 | 9/1999 |
| 2002/0147406 A1 | 10/2002 | von Segesser | | WO | WO99/55223 | 11/1999 |
| 2002/0151770 A1 | 10/2002 | Noll, III et al. | | WO | WO99/55225 | 11/1999 |
| 2002/0183628 A1 | 12/2002 | Reich et al. | | WO | WO99/59460 | 11/1999 |
| 2002/0188323 A1 | 12/2002 | Penner et al. | | WO | WO99/66988 | 12/1999 |
| 2003/0009204 A1 | 1/2003 | Amundson et al. | | WO | WO00/16686 | 3/2000 |
| 2003/0114897 A1 | 6/2003 | Von Arx et al. | | WO | WO00/58744 | 10/2000 |
| 2003/0136417 A1 | 7/2003 | Fonseca et al. | | WO | WO01/28627 | 4/2001 |
| 2003/0181794 A1 | 9/2003 | Rini et al. | | WO | WO01/56467 | 8/2001 |
| 2003/0191383 A1 | 10/2003 | Ben-Haim et al. | | WO | WO01/74278 | 10/2001 |
| 2004/0044393 A1 | 3/2004 | Yarden et al. | | WO | WO02/03347 | 1/2002 |
| 2004/0064133 A1 | 4/2004 | Miller et al. | | WO | WO02/32502 | 4/2002 |
| 2004/0077937 A1 | 4/2004 | Yarden | | WO | WO03/002243 | 1/2003 |

| | | | | | | |
|---|---|---|---|---|---|---|
| WO | WO03/096889 | 11/2003 | | WO | WO2007/030474 | 3/2007 |
| WO | WO2005/118056 | 12/2005 | | WO | WO2007/047287 | 4/2007 |
| WO | WO2006/033812 | 3/2006 | | WO | WO2007/070794 | 6/2007 |
| WO | WO2006/034183 | 3/2006 | | WO | WO2008/011592 | 1/2008 |
| WO | WO2006/045073 | 4/2006 | | WO | WO2008/011593 | 1/2008 |
| WO | WO2006/045074 | 4/2006 | | WO | WO2008/154145 | 12/2008 |
| WO | WO2006/045075 | 4/2006 | | | | |
| WO | WO2006/069215 | 6/2006 | | | | |

\* cited by examiner

DEVICES FOR INTRABODY DELIVERY OF MOLECULES AND SYSTEMS AND METHODS UTILIZING SAME

RELATED APPLICATIONS

This Application is a continuation of U.S. application Ser. No. 09/930,455, filed Aug. 16, 2001, now abandoned. This Application is also a continuation-in-part of U.S. application Ser. No. 10/235,968, filed Sep. 6, 2002, now U.S. Pat. No. 6,720,709, which is a continuation of U.S. application Ser. No. 09/691,887, filed Oct. 20, 2000, now U.S. Pat. No. 6,504,286, which is a continuation of U.S. application Ser. No. 09/000,553, filed Dec. 30, 1997, now U.S. Pat. No. 6,140,740, all of which are incorporated by reference herein in their entireties.

FIELD AND BACKGROUND OF THE INVENTION

The present invention relates to a device for intrabody delivery of molecules, to a method and system of utilizing same and to a method of fabricating same. More particularly, embodiments of the present invention relate to a drug delivery device which utilizes an acoustic transducer for generating an electrical activation signal from an acoustic signal received thereby.

The efficacy of drug treatment is oftentimes dependent upon the mode of drug delivery.

Localized drug delivery is oftentimes preferred since it traverses limitations associated with systemic drug delivery including rapid drug inactivation and/or ineffectual drug concentrations at the site of treatment. In addition, in some cases, systemic drug delivery can lead to undesired cytotoxic effects at tissue regions other than that to be treated.

Since localized intrabody delivery of medication is central to efficient medical treatment attempts have been made to design and fabricate intrabody delivery devices which are capable of controlled and localized release of a wide variety of molecules including, but not limited to, drugs and other therapeutics.

Controlled release polymeric devices have been designed to provide drug release over a period of time via diffusion of the drug out of the polymer and/or degradation of the polymer over the desired time period following administration to the patient. Although these devices enable localized drug delivery, their relatively simple design is limited in that it does not enable accurate and controlled delivery of the drug.

U.S. Pat. No. 5,490,962 to Cima, et al. discloses the use of three dimensional printing methods to make more complex devices which provide release over a desired time frame, of one or more drugs. Although the general procedure for making a complex device is described, specific designs are not detailed.

U.S. Pat. No. 4,003,379 to Ellinwood describes an implantable electromechanically driven device that includes a flexible retractable walled container, which receives medication from a storage area via an inlet and then dispenses the medication into the body via an outlet.

U.S. Pat. Nos. 4,146,029 and 3,692,027 to Ellinwood disclose self-powered medication systems that have programmable miniaturized dispensing means.

U.S. Pat. No. 4,360,019 to Jassawalla discloses an implantable infusion device that includes an actuating means for delivery of the drug through a catheter. The actuating means includes a solenoid driven miniature pump.

Since such devices include miniature power-driven mechanical parts which are required to operate in the body, i.e., they must retract, dispense, or pump, they are complicated and subject to frequent breakdowns. Moreover, due to complexity and size restrictions, they are unsuitable for delivery of more than a few drugs or drug mixtures at a time.

U.S. Pat. Nos. 6,123,861 and 5,797,898 both to Santini, Jr., et al. disclose microchips devices which control both the rate and time of release of multiple chemical substances either in a continuous or a pulsatile manner. Such microchip devices employ a reservoir cap which is fabricated of a material that either degrades or allows the molecules to diffuse passively out of the reservoir over time or materials that oxidize and dissolve upon application of an electric potential. Release from the microchip device can be controlled by a preprogrammed microprocessor, via a radiofrequency (RF) activation signal, or by biosensors.

Although the microchip device described by Santini, Jr., et al. presents substantial improvements over other prior art devices, it suffers from several inherent limitations which will be described in detail hereinbelow.

There is thus a widely recognized need for, and it would be highly advantageous to have, a delivery device and methods of fabricating and utilizing same which device can be used for accurate and timely delivery of a drug or drugs within a body tissue region devoid of the above limitation.

SUMMARY OF THE INVENTION

According to one aspect of the present invention there is provided a device for controlled release of molecules comprising: (a) a device body having at least one reservoir therein for containing the molecules, the at least one reservoir being formed with a barrier impermeable to the molecules thereby preventing release thereof from the at least one reservoir; and (b) at least one acoustic transducer being attached to, or forming a part of, the device body, the at least one acoustic transducer being for converting an acoustic signal received thereby into an electrical signal, the electrical signal leading to barrier permeabilization and therefore release of the molecules from the at least one reservoir.

According to an additional aspect of the present invention there is provided system for localized delivery of molecules within the body comprising: (a) an intrabody implantable device including: (i) a device body having at least one reservoir therein for containing the molecules, the at least one reservoir being formed with a barrier impermeable to the molecules thereby preventing release thereof from the at least one reservoir; and (ii) at least one acoustic transducer being attached to, or forming a part of, the device body, the at least one acoustic transducer being for converting an acoustic signal received thereby into an electrical signal, the electrical signal leading to barrier permeabilization and therefore release of the molecules from the at least one reservoir; and (b) an extracorporeal unit for generating the acoustic signal.

According to another aspect of the present invention there is provided a method of delivering molecules to a specific body region, the method comprising: (a) implanting within the body region a device including: (i) a device body having at least one reservoir therein containing the molecules, the at least one reservoir being formed with a barrier impermeable to the molecules thereby preventing release thereof from the at least one reservoir; and (ii) at least one acoustic transducer being attached to, or forming a part of, the device body, the at least one acoustic transducer being for converting an acoustic signal received thereby into an electrical signal, the electrical signal leading to barrier permeabilization and therefore release of the molecules from the at least one reservoir; and (b) extracorporeally irradiating the body with an acoustic signal thereby causing the subsequent release of the molecules from the at least one reservoir.

According to further features in preferred embodiments of the invention described below, the device further comprising a cathode, and an anode, whereas the electrical signal generates an electric potential between the cathode and the anode leading to permeabilization of the barrier and release of the molecules from the at least one reservoir.

According to still further features in the described preferred embodiments the anode is attached to or forms at least a part of the barrier.

According to still further features in the described preferred embodiments the electrical signal directly generates the electric potential between the cathode and the anode.

According to still further features in the described preferred embodiments the device further comprising a power source for generating the electric potential between the cathode and the anode upon receiving the electrical signal from the at least one acoustic transducer.

According to still further features in the described preferred embodiments the at least one acoustic transducer serves as an acoustic switch.

According to still further features in the described preferred embodiments permeabilization of the barrier is effected by at least partial disintegration thereof.

According to still further features in the described preferred embodiments a type or duration of the electrical signal controls a degree of permeabilization of the barrier and thus an amount of the molecules released.

According to still further features in the described preferred embodiments the device includes a plurality of reservoirs.

According to still further features in the described preferred embodiments the device includes a plurality of acoustic transducers.

According to still further features in the described preferred embodiments each of the plurality of acoustic transducers generates an electrical signal which leads to permeabilization of a barrier of a corresponding reservoir of the plurality of reservoirs.

According to still further features in the described preferred embodiments each of the plurality of acoustic transducers is capable of converting an acoustic signal of a distinct frequency or frequencies into the electrical signal.

According to still further features in the described preferred embodiments the plurality of reservoirs are for containing different types of molecules, different amounts of molecules, or combinations thereof.

According to still further features in the described preferred embodiments the molecules are drug molecules.

According to still further features in the described preferred embodiments the at least one acoustic transducer includes: (i) a cell member having a cavity; (ii) a substantially flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave; and (iii) a first electrode attached to the external surface and a second electrode attached to the internal surface.

According to still further features in the described preferred embodiments the device includes a plurality of reservoirs each containing molecules of a specific type and each capable of releasing the molecules upon provision of an acoustic signal of a specific frequency or frequencies, such that a frequency content of the acoustic signal determines a type of the molecules released.

According to an additional aspect of the present invention there is provided a device for controlled drug release comprising: (a) a device body including at least one reservoir being for containing a prodrug form of a drug, the at least one reservoir being formed with a barrier impermeable to the prodrug thereby preventing release thereof from the at least one reservoir; and (b) at least one acoustic transducer being attached to, or forming a part of the device body, the at least one acoustic transducer being for converting an acoustic signal received thereby into an electrical signal, the electrical signal leading to a conversion of the prodrug into the drug, the drug being capable of traversing the barrier thereby releasing from the at least one reservoir.

According to yet an additional aspect of the present invention there is provided a system for localized delivery of molecules within the body comprising: (a) an intrabody implantable device including: (i) a device body including at least one reservoir being for containing a prodrug form of a drug, the at least one reservoir being formed with a barrier impermeable to the prodrug thereby preventing release thereof from the at least one reservoir; and (ii) at least one acoustic transducer being attached to, or forming a part of the device body, the at least one acoustic transducer being for converting an acoustic signal received thereby into an electrical signal, the electrical signal leading to a conversion of the prodrug into the drug, the drug being capable of traversing the barrier thereby releasing from the at least one reservoir; and (b) an extracorporeal unit for generating the acoustic signal.

According to still further features in the described preferred embodiments a type or duration of the electrical signal controls a degree of the conversion and thus an amount of the drug formed and released.

According to still further features in the described preferred embodiments the device includes a plurality of reservoirs and a plurality of acoustic transducers, each of the plurality of acoustic transducers generates an electrical signal which leads to the conversion of the prodrug to the drug contained in a corresponding reservoir of the plurality of reservoirs.

According to still further features in the described preferred embodiments the plurality of reservoirs are for containing different types of prodrugs, different amounts of prodrugs, or combinations thereof.

According to still an additional aspect of the present invention there is provided a method of fabricating a device for controllable release of molecules, the method comprising: (a) providing a substrate; (b) configuring the substrate with at least one reservoir; (c) capping the at least one reservoir with a cap material which acts as an impermeable barrier to the molecules, the material becoming permeable to the molecules following generation of an electrical potential in or around the at least one reservoir; and (d) providing an inlet port for filling the at least on reservoir with the molecules, the inlet being sealable following the filling, thereby generating the device for controllable release of molecules.

According to still further features in the described preferred embodiments the method further comprising the step of: (e) attaching to, or fabricating within, the substrate, at least one acoustic transducer, the at least one acoustic transducer being for generating an electrical signal from an acoustic signal received thereby, the electrical signal leading to generation of the electrical potential in or around the at least one reservoir.

According to still further features in the described preferred embodiments the at least one acoustic transducer includes: (i) a cell member having a cavity; (ii) a substantially flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave; and (iii) a first electrode attached to the external surface and a second electrode attached to the internal surface.

According to still further features in the described preferred embodiments step (b) is effected by etching the substrate.

The present invention successfully addresses the shortcomings of the presently known configurations by providing a device, system and method for efficient intrabody delivery of molecules such as drugs as well as a method of manufacture.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
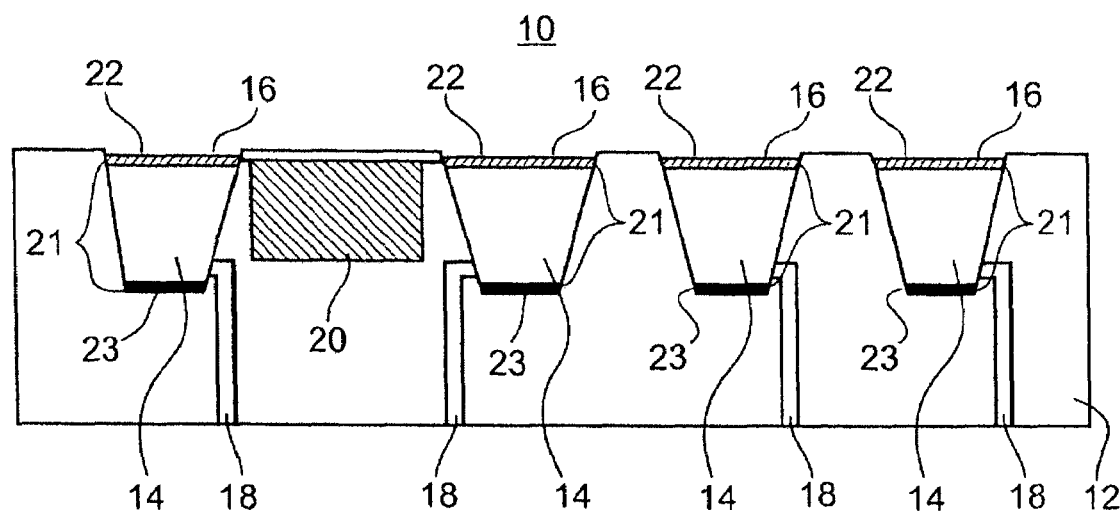
FIG. 1 is a cross sectional view of a general configuration of the device of the present invention.

The present invention is of a device, system and method which can be used for localized intrabody delivery of molecules. Specifically, the present invention can be used to release molecules such as drugs within a specific body region using an acoustic activation signal provided from outside the body.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates the device for controlled release of molecules, which is referred to herein as device 10.

Device 10 includes a device body 12 having at least one reservoir 14 formed therein for containing the molecules to be delivered.

Preferably, device body 12 includes a plurality of reservoirs 14 (four shown in FIG. 1) each being configured for containing therapeutic molecules such as drugs and/or diagnostic molecules such as dyes preferably in a solution or as a suspension. Reservoirs 14 can be of various dimensions depending on the molecule type and quantity to be delivered therefrom.

Device body 12 can be of a planar shape, spheroidal shape or any shape suitable for intrabody implantation and delivery of molecules stored thereby. Reservoirs 14 can be formed within a surface of device body 12 or within an interior volume thereof, provided molecules released therefrom can disperse into a medium surrounding device 10.

The dimensions of device 10 are limited by the site of implantation and delivery, the quantity of drugs or drugs to be delivered thereby, and the specific components used thereby for drug release activation.

Reservoirs 14 can be formed within device body 12 using any method known in the art including, but not limited to, etching, machining and the like. Alternatively, device body 12 may be pre-formed with reservoirs 14 by, for example, casting or milling techniques.

Device body 12 is fabricated from a material which is impermeable to the molecules to be delivered and to the surrounding fluids, for example, water, blood, electrolytes or other solutions. Examples of suitable materials include ceramics, semiconductors, biological membranes, and degradable and non-degradable polymers; biocompatibility is preferred, but not required.

For in-vivo applications, non-biocompatible materials may be encapsulated in a biocompatible material, such as polyethyleneglycol or polytetrafluoroethylene-like materials, before use. One example of a strong, non-degradable, easily etched substrate that is impermeable to the molecules to be delivered and the surrounding fluids is silicon.

Alternatively, device body 12 can also be fabricated from a material which degrades or dissolves over a period of time into biocompatible components such as Polyvinyl Alcohol (PVA). This embodiment is preferred for in vivo applications where the device is implanted and physical removal of the device at a later time is not feasible or recommended, as is the case with, for example, brain implants. An example of a class of strong, biocompatible materials are the poly(anhydride-co-imides) discussed by K. E. Uhrich et al., "Synthesis and characterization of degradable poly(anhydride-co-imides)", Macromolecules, 1995, 28, 2184-93.

Reservoir 14 is formed (capped) with a barrier 16 which is impermeable to the molecules to be delivered. As such barrier 16 serves for preventing molecules contained within reservoir 14 from releasing into the surrounding medium when device 10 is implanted within the body.

Reservoir 14 can be filled with molecules of interest either prior to capping with barrier 16 or following such capping. In the latter case, reservoir 14 also includes an inlet port 18, which serves for filling reservoir 14 with molecules of choice following fabrication of device 10. Inlet port 18 is designed to be sealable following filling, such that accidental drug release therefrom does not occur.

Device 10 further includes at least one acoustic transducer 20. Acoustic transducer 20 can be attached to, or it can form a part of, device body 12. Acoustic transducer 20 serves for converting an acoustic signal received thereby into an electrical signal. The electrical signal generated by transducer 20 is preferably rectified via a full or half-bridge rectifier into a DC current signal. The converted electrical signal can be used to directly or indirectly release the molecules stored in reservoir 14 as described hereinbelow.

According to a preferred embodiment of the present invention, the electrical signal generates (directly or indirectly) an electrical potential within reservoir 14.

To this end, device 10 further includes at least one pair of electrodes 21, which are preferably positioned within reservoir 14 and which serve for providing the electrical potential therein.

According to one preferred embodiment of the present invention, the electrical potential converts the molecules stored within reservoir 14 into an active and barrier permeable form.

For example, the molecules contained within reservoir 14 can be provided as large aggregates which are unable to traverse barrier 16 which can be, in this case, a size selective membrane. Upon provision of the electrical potential the molecules disaggregate into smaller active units which are able to diffuse out of reservoir 14 through barrier 16.

According to another preferred embodiment of the present invention, the electrical potential leads to permeabilization of barrier 16 and subsequent release of the molecules from reservoir 14.

For example, the electrical potential generated by electrodes 21 can cause the partial or full disintegration of barrier 16 and as such the release of the molecules from reservoir 14.

In such a case, barrier 16 can be composed of a thin film of conductive material that is deposited over the reservoir, patterned to a desired geometry, and function as an anode 22. The size and placement of cathode 23 depends upon the device's application and method of electric potential control.

Conductive materials capable of dissolving into solution or forming soluble compounds or ions upon the application of an electric potential, include, but are not limited to, metals such as copper, gold, silver, and zinc and some polymers.

Thus, according to this configuration of device 10, when an electric potential is applied between anode 22 and cathode 23, the conductive material of the anode above the reservoir oxidizes to form soluble compounds or ions that dissolve into solution, exposing the molecules to be delivered to the surrounding medium.

Alternatively, the application of an electric potential can be used to create changes in local pH near barrier 16 thereby leading to dissolving of barrier 16 and release of the molecules.

Still alternatively, the application of an electric potential can be used to create changes in the net charge of barrier 16 or the net charge or solubility of the molecules thereby enabling barrier 16 traversing.

In any case, the molecules to be delivered are released into the surrounding medium by diffusion out of or by degradation or dissolution of the release system. The frequency and quantity of release can be controlled via the acoustic signal received by acoustic transducer 20 as is further described hereinbelow.

Figure 2:
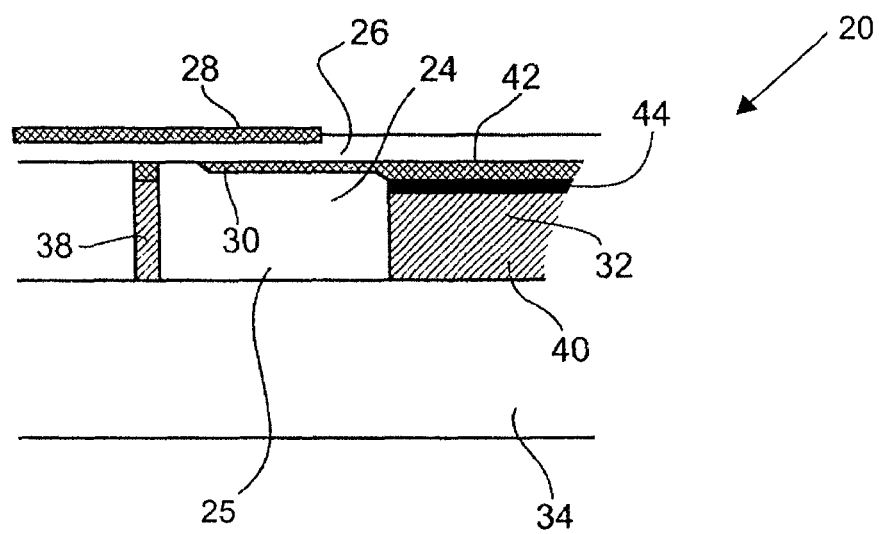
FIGS. 2-3 illustrate cross sectional views of a prior art transducer element utilizable by the device of the present invention.
Figure 3:
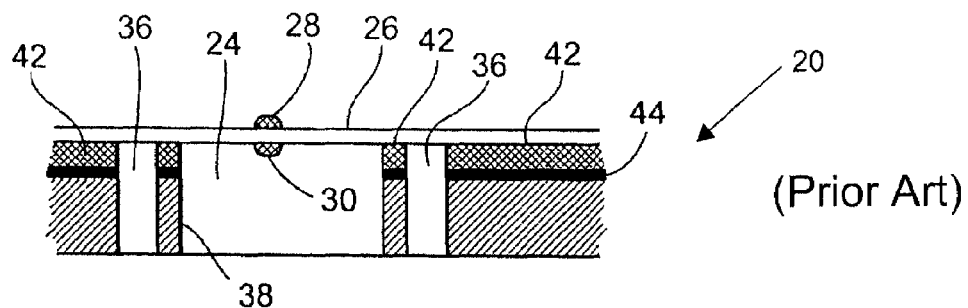

According to a preferred embodiment of the present invention and as specifically shown in FIGS. 2-3, acoustic transducer 20 includes at least one cell member 25 including a cavity 24 etched or drilled into a substrate and covered by a substantially flexible piezoelectric layer 26. Attached to piezoelectric layer 26 are an upper electrode 28 and a lower electrode 30 which are connectable to an electronic circuit. The substrate is preferably made of an electrical conducting layer 32 disposed on an electrically insulating layer 34, such that cavity 24 is etched substantially through the thickness of electrically conducting layer 32. Electrically conducting layer 32 is preferably made of copper and insulating layer 34 is preferably made of a polymer such as polyimide. Conventional copper-plated polymer laminate such as KAPTON sheets may be used for the production of transducer 20. Commercially available laminates such as NOVOCLAD may be used. Alternatively, the substrate may include a silicon layer, or any other suitable material. Alternatively, layer 32 is made of a non-conductive material such as PYRALIN.

An insulating chamber 36 is etched into the substrate, preferably through the thickness of conducting layer 32, so as to insulate the transducer element from other portions of the substrate which may include other electrical components such as other transducer elements etched into the substrate.

According to a specific embodiment, the width of insulating chamber 36 is about 100 µm. As shown, insulating chamber 36 is etched into the substrate so as to form a wall 38 of a predetermined thickness enclosing cavity 24, and a conducting line 40 integrally made with wall 38 for connecting the transducer element to another electronic component preferably etched into the same substrate, or to an external electronic circuit.

Upper electrode 28 and lower electrode 30 are preferably precisely shaped, so as to cover a predetermined area of piezoelectric layer 26. Electrodes 28 and 30 may be deposited on the upper and lower surfaces of piezoelectric layer 26, respectively, by using various methods such as vacuum deposition, mask etching, painting, and the like.

Lower electrode 30 is preferably made as an integral part of a substantially thin electrically conducting layer 42 disposed on electrically conducting layer 32. Preferably, electrically conducting layer 42 is made of a Nickel-Copper alloy and is attached to electrically conducting layer 32 by means of a sealing connection 44. Sealing connection 44 may be made of chemical or physical metal vapour deposition (CVD or PVD) indium. According to a preferred configuration, sealing connection 44 may feature a thickness of about 10 µm, such that the overall height of wall 38 of cavity 24 is about 20-25 µm.

Preferably, cavity 24 is etched or drilled into the substrate by using conventional printed-circuit photolithography methods. Alternatively, cavity 24 may be etched into the substrate by using VLSI/micro-machining technology or any other suitable technology. Cavity 24 preferably includes a gas such as air. The pressure of gas within cavity 24 may be specifically selected so as to predetermine the sensitivity and ruggedness of the transducer as well as the resonant frequency of layer 26. Piezoelectric layer 26 may be made of PVDF or a copolymer thereof. Alternatively, piezoelectric layer 26 is made of a substantially flexible piezoceramic. Preferably, piezoelectric layer 26 is a poled PVDF sheet having a thickness of about 9-28 µm. Preferably, the thickness and radius of flexible layer 26, as well as the pressure within cavity 24, are specifically selected so as to provide a predetermined resonant frequency.

The use of a substantially flexible piezoelectric layer 26, allows to produce a miniature transducer element whose resonant frequency is such that the acoustic wavelength is much larger than the extent of the transducer. This enables the transducer to be omnidirectional even at resonance, and further allows the use of relatively low frequency acoustic signals which do not suffer from significant attenuation in the surrounding medium.

The configuration and acoustic properties of such an acoustic transducer and variants thereof as well as general acoustic transduction principles are described in detail in U.S. patent application Ser. No. 09/000,553 and PCT Publication No. WO 99/34,453 the disclosures of which are expressly incorporated by reference as if fully set forth herein.

As mentioned hereinabove, the electrical signal generated by acoustic transducer 20 can directly or indirectly activate the release of the molecules from reservoir 20.

Figure 4:
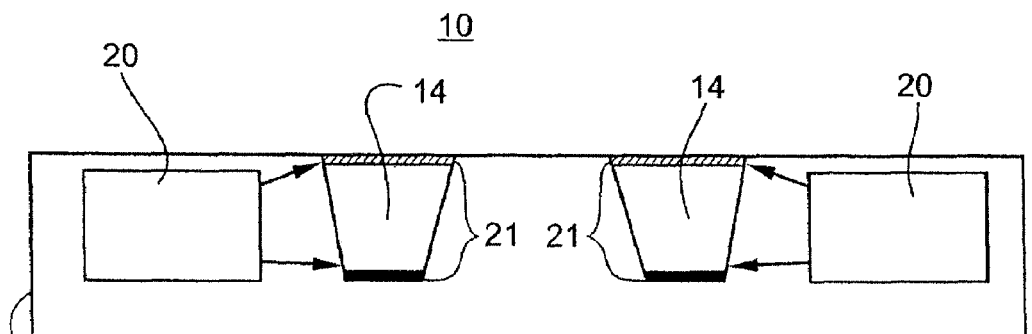
FIG. 4 illustrates a "direct activation" configuration of the device of the present invention.

In the direct embodiment of device 10 which is specifically shown in FIG. 4, the electrical signal generated by acoustic transducer 20 is communicated directly (via circuitry) to electrodes 21 to thereby generate the electrical potential.

It will be appreciated that in such cases, the degree of barrier permeabilization and as such the degree of drug release can be controlled by the duration and/or frequency of the acoustic signal and/or its intensity received by acoustic transducer 20.

It will further be appreciated that in cases where device 10 includes a plurality of reservoirs, several acoustic transducers can be utilized such that various activation schemes can be employed.

For example, device 10 can include a plurality of acoustic transducers 20 each dedicated to a specific reservoir of reservoirs 14. In such a case, each acoustic transducer 20 can function within a specific frequency range and as such activate release from a specific reservoir 14 only upon reception of an acoustic signal of the specific frequency of frequency range.

Such a configuration enables selective activation of specific reservoirs enabling control over the amount and rate of molecules released as well as enabling control over the type of molecules released, in cases where specific molecules are stored within specific reservoirs.

Figure 5:
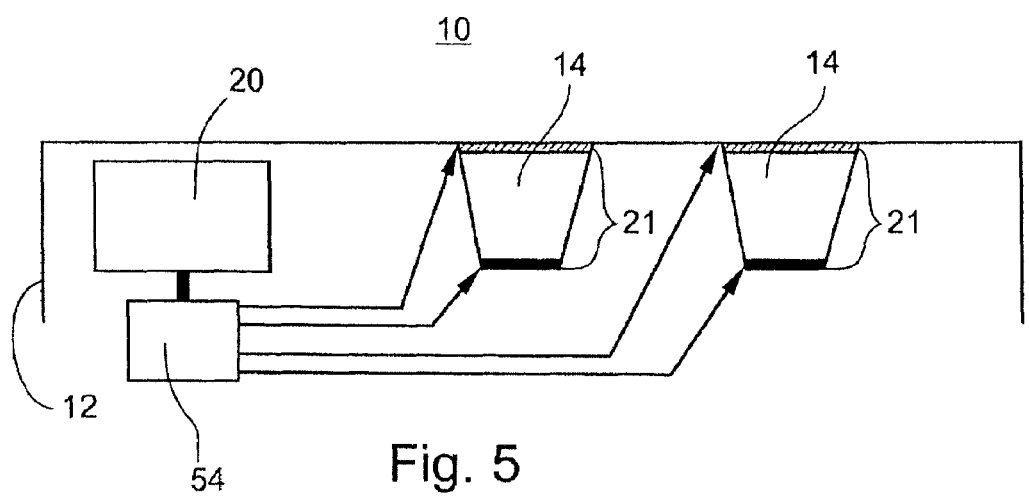
FIG. 5 illustrates an "indirect activation" configuration of the device of the present invention.

In the indirect embodiment of device 10 which is specifically shown in FIG. 5, the electrical signal generated by acoustic transducer 20 serves to activate an energy storage device 54 which in turn generates the electrical potential between electrodes 21.

In such cases, acoustic transducer 20 preferably forms a part of an acoustic switch 50 which can be configured as described below.

Figure 6:
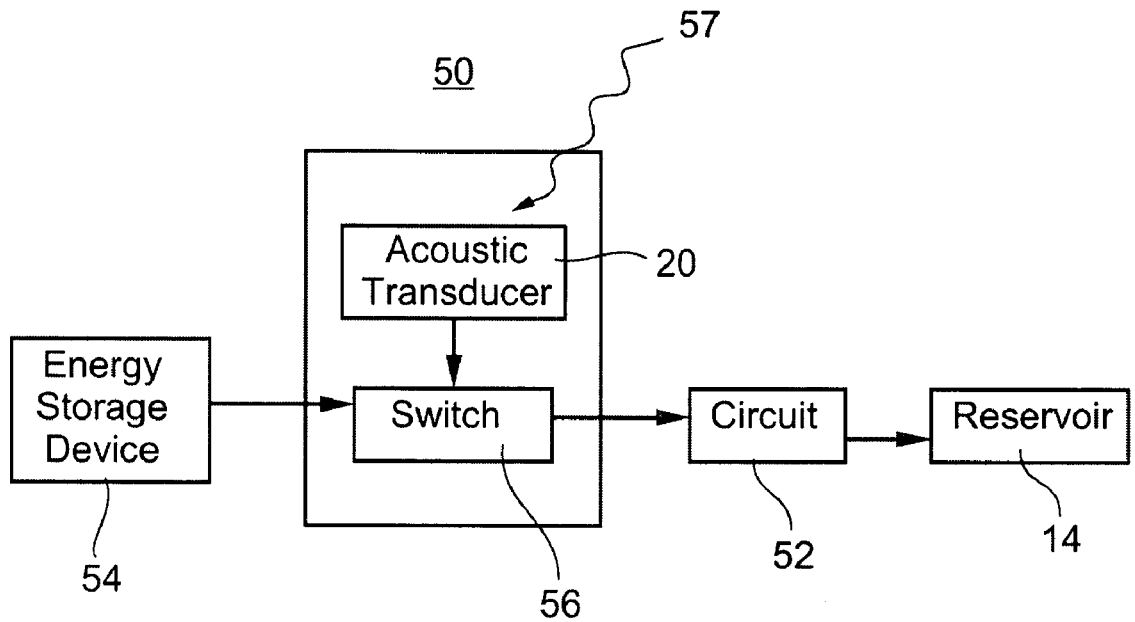
FIG. 6 is a schematic diagram illustrating an acoustic switch utilizable by the device of the present invention.

As specifically shown in FIG. 6, acoustic switch 50 includes an electrical circuit 52 configured for performing one or more functions or commands when activated.

Acoustic switch 50 further includes an energy storage device 54 (power source) and an acoustic transducer 20 coupled to electrical circuit 52 and energy storage device 54.

In addition, acoustic switch 50 also includes a switch 56, such as the switch described in the Examples section below, although alternatively other switches, such as a miniature electromechanical switch and the like (not shown) may be provided.

Energy storage device 54 may be any of a variety of known devices, such as an energy exchanger, a battery and/or a capacitor (not shown). Preferably, energy storage device 54 is capable of storing electrical energy substantially indefinitely. In addition, energy storage device 54 may be capable of being charged from an external source, e.g., inductively, as will be appreciated by those skilled in the art. In a preferred embodiment, energy storage device 54 includes both a capacitor and a primary, non-rechargeable battery. Alternatively, energy storage device 54 may include a secondary, rechargeable battery and/or capacitor that may be energized before activation or use of acoustic switch 50.

Acoustic switch 50 operates in one of two modes, a "sleep" or "passive" mode when not in use, and an "active" mode, when commanding electrical energy delivery from energy storage device 54 to electrical circuit 52 in order to activate release of molecules from reservoir 14 as described hereinabove.

When in the sleep mode, there is substantially no energy consumption from energy storage device 54, and consequently, acoustic switch 50 may remain in the sleep mode virtually indefinitely, i.e., until activated. Thus, acoustic switch 50 may be more energy efficient and, therefore, may require a smaller capacity energy storage device 54 than power switching devices that continuously draw at least a small amount of current in their "passive" mode.

To activate the acoustic switch, one or more external acoustic energy waves or signals 57 are transmitted until a signal is received by acoustic transducer 20. Upon excitation by acoustic wave(s) 57, acoustic transducer 20 produces an electrical output that is used to close, open, or otherwise activate switch 56. Preferably, in order to achieve reliable switching, acoustic transducer 20 is configured to generate a voltage of at least several tenths of a volt upon excitation that may be used as an activation signal to close switch 56.

As a safety measure against false positives (either erroneous activation or deactivation), switch 56 may be configured to close only upon receipt of an initiation signal followed by a confirmation signal. For example, an activation signal that includes a first pulse followed by a second pulse separated by a predetermined delay may be employed.

It will be appreciated that in the case of device 10 of the present invention, the use of a confirmation signal may be particularly advantageous since it can prevent unintentional release of drugs.

In addition to an activation signal, acoustic transducer 20 may be configured for generating a termination signal in response to a second acoustic excitation (which may be of different frequency or duration than the activation signal) in order to return acoustic switch 50 to its sleep mode.

For example, once activated, switch 56 may remain closed indefinitely, e.g., until energy storage device 54 is depleted or until a termination signal is received by acoustic transducer 20. Alternatively, acoustic switch 50 may include a timer (not shown), such that switch 56 remains closed only for a predetermined time, whereupon it may automatically open, returning acoustic switch 50 to its sleep mode.

Acoustic switch may also include a microprocessor unit which serves to interpret the electrical signal provided from acoustic transducer 20 (e.g., frequency thereof) into a signal for switching switch 56.

Such interpretation enables to modulate the duration and strength of an electrical potential provided within reservoir 14 by simply varying the frequency and/or duration and/or intensity modulation of the acoustic signal provided from outside the body.

Additional acoustic switch configurations which are utilizable by the present invention are described in U.S. patent application Ser. No. 09/690,615 filed Oct. 16, 2000, the disclosure of which is expressly incorporated by reference as if fully set forth herein.

Device 10 of the present invention can form a part of a system for localized release of, for example, drugs, which is referred to herein as system 100.

Figure 7:
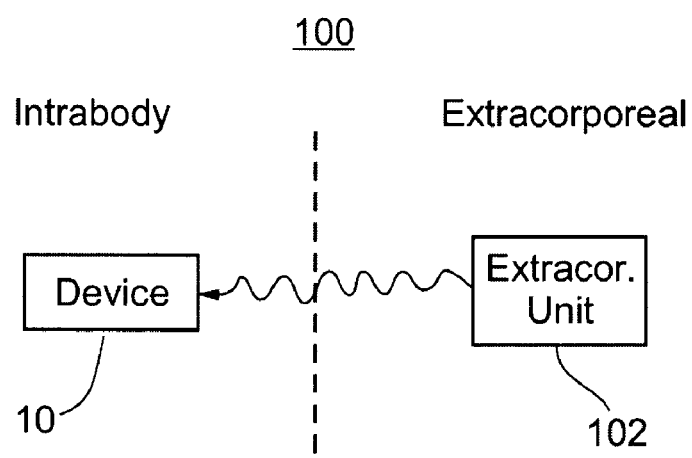
FIG. 7 is a black box diagram of a drug delivery system according to the teachings of the present invention.

As shown in FIG. 7, system 100 also includes an extracorporeal unit 102 which serves for generating an acoustic signal outside the body, which acoustic signal is received by device 10 implanted within the body. Numerous devices capable of generating acoustic signal which can serve as extracorporeal unit 102 are known in the art, and as such no further description thereof is given herein.

System 100 can be used as follows. A device 10 filled with molecules is implanted within a specific body tissue. Following implantation, extracorporeal unit 102 generates an acoustic signal of a predetermined frequency and/or duration thereby activating release of the molecules from device 10 as described hereinabove.

Thus, the present invention provides a device, system and method useful for localized delivery of molecules such as drugs.

The device of the present invention provides several advantages over prior art devices such as those described in U.S. Pat. Nos. 6,123,861 and 5,797,898. Such advantages are afforded by the acoustic transducer component of the device which functions in converting an acoustic signal into an electrical activation signal.

In sharp contrast, the device described in U.S. Pat. Nos. 6,123,861 and 5,797,898, employs radiofrequency (RF) receivers which activate drug release upon reception of an RF signal generated outside the body. The use of RF activation is disadvantageous since RF signals are, at least in part, absorbed by body tissues and are directionally limited by bulky unidirectional antennas used for reception.

On the other hand, acoustic transducers, such as the one utilized by the device of the present invention, are omnidirectional receivers which do not require antennas and as such do not suffer from structural and functional limitations which are inherent to RF receivers.

In addition, acoustic activation requires far less energy than RF activation since acoustic waves, unlike RF waves, propagate well within the aqueous medium which forms a substantial part of body tissues.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Acoustic Switch Circuitry and Function

Figure 8:
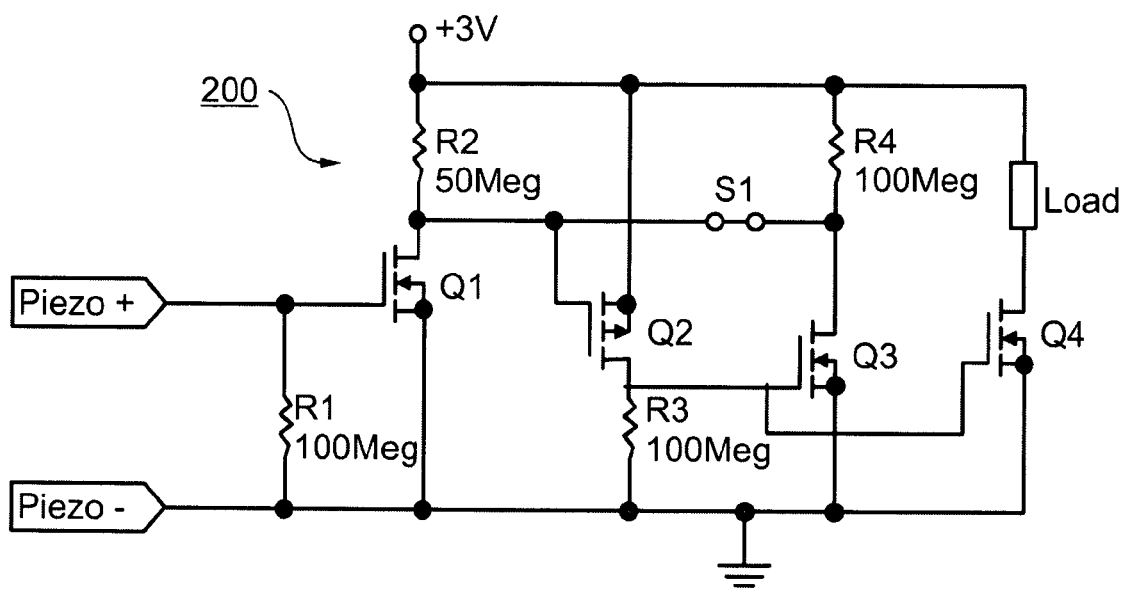
FIG. 8 is schematic diagram illustrating a control circuitry of the acoustic switch illustrated in FIG. 6.

Referring again to the drawings, FIG. 8, illustrates an example of circuitry and components employed by an acoustic switch 200 which is utilizable by the device of the present invention.

Switch 200 includes a piezoelectric transducer, or other acoustic transducer such the acoustic transducer described hereinabove (not shown, but connectable at locations piezo + and piezo −), a plurality of MOSFET transistors (Q1-Q4) and resistors (R1-R4), and switch S1.

In the switch's "sleep" mode, all of the MOSFET transistors (Q1-Q4) are in an off state. To maintain the off state, the gates of the transistors are biased by pull-up and pull-down resistors. The gates of N-channel transistors (Q1, Q3 & Q4) are biased to ground and the gate of P-channel transistor Q2 is biased to +3V. During this quiescent stage, switch S1 is closed and no current flows through the circuit.

Therefore, although an energy storage device (not shown, but coupled between the hot post, labeled with an exemplary voltage of +3V, and ground) is connected to the switch 200, no current is being drawn therefrom since all of the transistors are quiescent.

When the piezoelectric transducer detects an external acoustic signal, e.g., having a particular frequency such as the transducer's resonant frequency, the voltage on the transistor Q1 will exceed the transistor threshold voltage of about one half of a volt. Transistor Q1 is thereby switched on and current flows through transistor Q1 and pull-up resistor R2. As a result of the current flow through transistor Q1, the voltage on the drain of transistor Q1 and the gate of transistor Q2 drops from +3V substantially to zero (ground). This drop in voltage switches on the P-channel transistor Q2, which begins to conduct through transistor Q2 and pull-down resistor R3.

As a result of the current flowing through transistor Q2, the voltage on the drain of transistor Q2 and the gates of transistors Q3 and Q4 increases from substantially zero to +3V. The increase in voltage switches on transistors Q3 and Q4. As a result, transistor Q3 begins to conduct through resistor R4 and main switching transistor Q4 begins to conduct through the "load," thereby switching on the electrical circuit.

As a result of the current flowing through transistor Q3, the gate of transistor Q2 is connected to ground through transistor Q3, irrespective of whether or not transistor Q1 is conducting. At this stage, the transistors (Q2, Q3 & Q4) are latched to the conducting state, even if the piezoelectric voltage on transistor Q1 is subsequently reduced to zero and transistor Q1 ceases to conduct. Thus, main switching transistor Q4 will remain on until switch S1 is opened.

In order to deactivate or open switch 200, switch S1 must be opened, for example, while there is no acoustic excitation of the piezoelectric transducer. If this occurs, the gate of transistor Q2 increases to +3V due to pull-up resistor R2. Transistor Q2 then switches off, thereby, in turn, switching off transistors Q3 and Q4. At this stage, switch 200 returns to its sleep mode, even if switch SI is again closed. Switch 200 will only return to its active mode upon receiving a new acoustic activation signal from the piezoelectric transducer.

It should be apparent to one of ordinary skill in the art that the above-mentioned electrical circuit is not the only possible implementation of a switch for use with the present invention. For example, the switching operation my be performed using a CMOS circuit, which may draw less current when switched on, an electromechanical switch, and the like.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention.

What is claimed is:

1. A device for controlled release of molecules comprising:
   (a) a device body having at least one reservoir therein for containing the molecules, said at least one reservoir being formed with a barrier impermeable to the molecules thereby preventing release thereof from said at least one reservoir;
   (b) at least one acoustic transducer being attached to, or forming a part of, said device body, said at least one acoustic transducer being for converting an acoustic signal received thereby into an electrical signal; and
   (c) an acoustic switch coupled between the at least one acoustic transducer and an energy storage device, the energy storage device adapted to supply current to an electrical circuit operably coupled to the at least one reservoir upon the acoustic transducer receiving an acoustic wake-up signal from an acoustic energy source, the acoustic switch configured to actuate the electrical circuit between a passive mode in which the current is limited from flowing from the energy storage device to the electrical circuit, and an active mode that allows current to flow from the energy storage device to the electrical circuit, wherein in the active mode current flows from the energy storage device to the electrical circuit leading to barrier permeabilization and therefore release of the molecules from the at least one reservoir.

2. The device of claim 1, further comprising a cathode and an anode, wherein in the active mode, the electrical circuit generates an electric potential between said cathode and said anode leading to permeabilization of said barrier and release of the molecules from said at least one reservoir.

3. The device of claim 2, wherein said anode is attached to or forms at least a part of said barrier.

4. The device of claim 1, wherein permeabilization of said barrier is effected by at least partial disintegration thereof.

5. The device of claim 1, wherein the device includes a plurality of reservoirs.

6. The device of claim 5, wherein the device includes a plurality of acoustic transducers.

7. The device of claim 6, wherein each of said plurality of acoustic transducers generates an electrical signal received by the electrical circuit which leads to permeabilization of a barrier of a corresponding reservoir of said plurality of reservoirs.

8. The device of claim 7, wherein each of said plurality of acoustic transducers is capable of converting an acoustic signal of a distinct frequency or frequencies into said electrical signal.

9. The device of claim 1, wherein said at least one acoustic transducer includes:
   (i) a cell member having a cavity;
   (ii) a substantially flexible piezoelectric layer attached to said cell member, said piezoelectric layer having an external surface and an internal surface, said piezoelectric layer featuring such dimensions so as to enable fluctuations thereof at its resonance frequency upon impinging of an external acoustic wave; and
   (iii) a first electrode attached to said external surface and a second electrode attached to said internal surface.

10. A method of delivering molecules to a specific body region, the method comprising:
    (a) implanting within the body region a device including:
    (i) a device body having at least one reservoir therein containing the molecules, said at least one reservoir being formed with a barrier impermeable to the molecules thereby preventing release thereof from said at least one reservoir; and
    (ii) at least one acoustic transducer being attached to, or forming a part of, said device body, said at least one acoustic transducer being for converting an acoustic signal received thereby into an electrical signal;
    (iii) an acoustic switch coupled between the acoustic transducer and an energy storage device, the energy storage device adapted to supply current to an electrical circuit operably coupled to the reservoir upon the acoustic transducer receiving an acoustic wake-up signal from an acoustic energy source, the acoustic switch configured to actuate the electrical circuit between a passive mode in which the current is limited from flowing from the energy storage device to the electrical circuit, and an active mode that allows current to flow from the energy storage device to the electrical circuit, wherein in the active mode current flows from the energy storage device to the electrical circuit leading to barrier permeabilization and therefore release of the molecules from the at least one reservoir; and
    (b) extracorporeally irradiating the body with an acoustic signal thereby causing the subsequent release of the molecules from said at least one reservoir.

11. The method of claim 10, wherein said device includes a plurality of reservoirs each containing molecules of a specific type and each capable of releasing said molecules upon provision of an acoustic signal of a specific frequency or frequencies, such that a frequency content of said acoustic signal determines a type of said molecules released.

12. The method of claim 10, wherein a frequency content or duration of said acoustic signal controls a degree of permeabilization of said barrier and thus an amount of the molecules released.

13. The method of claim 10, wherein said molecules are drug molecules.

14. The method of claim 10, wherein said device further includes a cathode, and an anode, wherein in the active mode, the electrical circuit generates an electric potential between said cathode and said anode leading to permeabilization of said barrier and release of the molecules from said at least one reservoir.

15. The method of claim 14, wherein said anode is attached to or forms at least a part of said barrier.

16. A system for localized delivery of molecules within the body, comprising:
    (a) an intrabody implantable device including:
    (i) a device body having at least one reservoir therein for containing the molecules, said at least one reservoir being formed with a barrier impermeable to the molecules thereby preventing release thereof from said at least one reservoir; and
    (ii) at least one acoustic transducer being attached to, or forming a part of, said device body, said at least one acoustic transducer being for converting an acoustic signal received thereby into an electrical signal
    (iii) an acoustic switch coupled between the acoustic transducer and an energy storage device, the energy storage device adapted to supply current to an electrical circuit operably coupled to the reservoir upon the acoustic transducer receiving an acoustic wake-up signal from an acoustic energy source, the acoustic switch configured to actuate the electrical circuit between a passive state in which the current is limited from flowing from the energy storage device to the electrical circuit, and an active state that allows current to flow from the energy storage device to the electrical circuit, wherein in the active state current flows from the energy storage device to the electrical circuit leading to barrier permeabilization and therefore release of the molecules from the at least one reservoir; and (b) an extracorporeal unit for generating said acoustic signal.

* * * * *

UNITED STATES PATENT AND TRADEMARK OFFICE
CERTIFICATE OF CORRECTION

PATENT NO. : 7,621,905 B2
APPLICATION NO. : 10/638405
DATED : November 24, 2009
INVENTOR(S) : Penner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1868 days.

Signed and Sealed this

Twenty-sixth Day of October, 2010

David J. Kappos
*Director of the United States Patent and Trademark Office*